(12) United States Patent
Harris et al.

(10) Patent No.: US 12,097,109 B2
(45) Date of Patent: Sep. 24, 2024

(54) ADJUSTABLE VASCULAR GRAFT FOR CUSTOM INNER DIAMETER REDUCTION AND RELATED METHODS

(71) Applicant: C. R. Bard, Inc., Franklin Lakes, NJ (US)

(72) Inventors: Keith Harris, Chandler, AZ (US); Kevin Boyle, Scottsdale, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 977 days.

(21) Appl. No.: 17/001,420

(22) Filed: Aug. 24, 2020

(65) Prior Publication Data

US 2020/0383768 A1 Dec. 10, 2020

Related U.S. Application Data

(63) Continuation of application No. 16/111,850, filed on Aug. 24, 2018, now Pat. No. 10,765,504, which is a
(Continued)

(51) Int. Cl.
*A61F 2/06* (2013.01)
*A61F 2/07* (2013.01)
(Continued)

(52) U.S. Cl.
CPC .................. *A61F 2/06* (2013.01); *A61F 2/07* (2013.01); *A61L 27/16* (2013.01); *A61L 27/56* (2013.01);
(Continued)

(58) Field of Classification Search
CPC ................ A61F 2/06; A61F 2220/0075; A61F 2250/0098
See application file for complete search history.

(56) References Cited

U.S. PATENT DOCUMENTS 3,538,917 A 11/1970 Selker
3,692,027 A 9/1972 Ellinwood, Jr.
(Continued)

FOREIGN PATENT DOCUMENTS

CA 2456046 A1 12/1999
DE 4037043 A1 5/1992
(Continued)

OTHER PUBLICATIONS

PCT/US2017/064137 Dec. 1, 2017, International Search Report and Written Opinion dated Jul. 10, 2018.
(Continued)

*Primary Examiner* — Carrie R Dorna
(74) *Attorney, Agent, or Firm* — Rutan & Tucker LLP

(57) ABSTRACT

An adjustable vascular graft with a user-customizable reduced inner diameter is provided. The graft includes a flexible tubular body having open ends and a plurality of receivers in a sidewall thereof, which may be arranged in two circumferentially spaced rows of receivers. The receivers may take the form of ringlets, eyelets, loops, or holes, which may be provided in a reinforced region of the graft sidewall, and which may be radiopaque. A suture passes through the plurality of receivers, the suture having first and second free ends capable of being pulled, and which suture may also be radiopaque. Tensioning or tightening the first and second ends of the suture reduces an inner diameter of the corresponding portion of the tubular body of the graft, thereby allowing for the custom reduced inner diameter and a resulting flow restriction to be provided. Related methods are also disclosed.

20 Claims, 7 Drawing Sheets

Related U.S. Application Data continuation of application No. PCT/US2017/064137, filed on Dec. 1, 2017.

(51) Int. Cl.
  *A61L 27/16* (2006.01)
  *A61L 27/56* (2006.01)
  *B29C 55/22* (2006.01)

(52) U.S. Cl.
  CPC ...... *B29C 55/22* (2013.01); *A61F 2220/0075* (2013.01); *A61F 2230/001* (2013.01); *A61F 2240/001* (2013.01); *A61F 2240/002* (2013.01); *A61F 2250/001* (2013.01); *A61F 2250/0036* (2013.01); *A61F 2250/0098* (2013.01)

(56) References Cited

U.S. PATENT DOCUMENTS

| | | | |
|---|---|---|---|
| 3,749,098 A | 7/1973 | De Bennetot | |
| 3,750,194 A | 8/1973 | Summers | |
| 3,810,259 A | 5/1974 | Summers | |
| 3,863,622 A | 2/1975 | Buuck | |
| 4,118,805 A | 10/1978 | Reimels | |
| 4,146,029 A | 3/1979 | Ellinwood, Jr. | |
| 4,200,119 A | 4/1980 | Cunningham | |
| 4,256,093 A | 3/1981 | Helms et al. | |
| 4,256,094 A | 3/1981 | Kapp et al. | |
| 4,390,019 A | 6/1983 | LeVeen et al. | |
| 4,487,567 A | 12/1984 | Possis et al. | |
| 4,546,499 A | 10/1985 | Possis et al. | |
| 4,562,597 A | 1/1986 | Possis et al. | |
| 4,601,718 A | 7/1986 | Possis et al. | |
| 4,828,544 A | 5/1989 | Lane et al. | |
| 4,909,979 A | 3/1990 | Possis et al. | |
| 5,089,014 A | 2/1992 | Holfert | |
| 5,197,978 A | 3/1993 | Hess | |
| 5,282,847 A | 2/1994 | Trescony et al. | |
| 5,464,449 A | 11/1995 | Ryan et al. | |
| 5,509,888 A | 4/1996 | Miller | |
| 5,556,426 A | 9/1996 | Popadiuk et al. | |
| 5,571,121 A | 11/1996 | Heifetz | |
| 5,591,226 A | 1/1997 | Trerotola et al. | |
| 5,609,626 A | 3/1997 | Quijano et al. | |
| 5,641,373 A * | 6/1997 | Shannon | B29D 23/001 |
| | | | 156/308.2 |
| 5,662,711 A | 9/1997 | Douglas | |
| 5,704,893 A | 1/1998 | Timm | |
| 5,769,877 A | 6/1998 | Barreras, Sr. | |
| 5,771,903 A | 6/1998 | Jakobsson | |
| 5,779,732 A | 7/1998 | Amundson | |
| 5,797,879 A | 8/1998 | DeCampli | |
| 5,824,061 A | 10/1998 | Quijano et al. | |
| 5,833,707 A | 11/1998 | McIntyre et al. | |
| 5,847,447 A | 12/1998 | Rozin et al. | |
| 5,876,433 A | 3/1999 | Lunn | |
| 5,879,320 A | 3/1999 | Cazenave | |
| 5,938,669 A | 8/1999 | Klaiber et al. | |
| 5,997,573 A | 12/1999 | Quijano et al. | |
| 6,019,788 A | 2/2000 | Butters et al. | |
| 6,022,374 A * | 2/2000 | Imran | A61F 2/91 |
| | | | 623/1.34 |
| 6,053,891 A | 4/2000 | DeCampli | |
| 6,162,537 A | 12/2000 | Martin et al. | |
| 6,174,330 B1 * | 1/2001 | Stinson | A61L 31/18 |
| | | | 606/198 |
| 6,221,066 B1 | 4/2001 | Ferrera et al. | |
| 6,235,051 B1 | 5/2001 | Murphy | |
| 6,270,523 B1 | 8/2001 | Herweck et al. | |
| 6,277,133 B1 | 8/2001 | Kanesaka | |
| 6,352,561 B1 | 3/2002 | Leopold et al. | |
| 6,371,953 B1 | 4/2002 | Beyar et al. | |
| 6,371,979 B1 | 4/2002 | Beyar et al. | |
| 6,450,989 B2 | 9/2002 | Dubrul et al. | |
| 6,470,892 B1 | 10/2002 | Forsell | |
| 6,494,904 B1 | 12/2002 | Love | |
| 6,531,964 B1 | 3/2003 | Loving | |
| 6,613,072 B2 * | 9/2003 | Lau | A61F 2/91 |
| | | | 623/1.2 |
| 6,692,521 B2 | 2/2004 | Pinchasik | |
| 6,827,731 B2 | 12/2004 | Armstrong et al. | |
| 6,860,898 B2 | 3/2005 | Stack et al. | |
| 6,929,011 B2 | 8/2005 | Knudson et al. | |
| 6,955,685 B2 | 10/2005 | Escamilla et al. | |
| 6,984,201 B2 | 1/2006 | Khaghani et al. | |
| 7,070,616 B2 | 7/2006 | Majercak et al. | |
| 7,101,390 B2 | 9/2006 | Nelson | |
| 7,108,673 B1 | 9/2006 | Batiste | |
| 7,121,999 B2 | 10/2006 | Abraham et al. | |
| 7,128,750 B1 | 10/2006 | Stergiopulos | |
| 7,198,636 B2 | 4/2007 | Cully et al. | |
| 7,252,680 B2 | 8/2007 | Freitag | |
| 7,270,675 B2 | 9/2007 | Chun et al. | |
| 7,297,156 B2 | 11/2007 | Nelson | |
| 7,320,703 B2 | 1/2008 | DiMatteo et al. | |
| 7,347,869 B2 | 3/2008 | Hojeibane et al. | |
| 7,351,256 B2 | 4/2008 | Hojeibane et al. | |
| 7,399,311 B2 | 7/2008 | Bertolino et al. | |
| 7,556,641 B2 | 7/2009 | Cully et al. | |
| 7,632,296 B2 | 12/2009 | Malewicz | |
| 7,901,455 B2 | 3/2011 | Koob et al. | |
| 7,993,369 B2 | 8/2011 | Dreyfuss | |
| 8,025,691 B2 | 9/2011 | Carter et al. | |
| 8,075,608 B2 | 12/2011 | Gordon et al. | |
| 8,079,974 B2 | 12/2011 | Stergiopulos | |
| 8,088,154 B2 | 1/2012 | Hoffman et al. | |
| 8,118,855 B2 | 2/2012 | Hartley et al. | |
| 8,231,668 B2 | 7/2012 | Friebe et al. | |
| 8,241,346 B2 | 8/2012 | Chobotov | |
| 8,398,700 B2 | 3/2013 | Leopold et al. | |
| 8,545,544 B2 | 10/2013 | Spenser et al. | |
| 8,568,466 B2 | 10/2013 | Shaolian et al. | |
| 10,765,504 B2 | 9/2020 | Harris et al. | |
| 2002/0013589 A1 | 1/2002 | Callister et al. | |
| 2002/0052660 A1 | 5/2002 | Greenhalgh | |
| 2002/0065546 A1 | 5/2002 | Machan et al. | |
| 2002/0065552 A1 | 5/2002 | Jayaraman et al. | |
| 2004/0064081 A1 | 4/2004 | Stanish | |
| 2004/0098090 A1 | 5/2004 | Williams et al. | |
| 2004/0116996 A1 | 6/2004 | Freitag | |
| 2005/0004653 A1 | 1/2005 | Gerberding et al. | |
| 2005/0038396 A1 | 2/2005 | Claude et al. | |
| 2005/0049668 A1 | 3/2005 | Jones et al. | |
| 2005/0113908 A1 | 5/2005 | Sweet et al. | |
| 2005/0137518 A1 | 6/2005 | Biggs et al. | |
| 2005/0222668 A1 | 10/2005 | Schaeffer et al. | |
| 2007/0043425 A1 | 2/2007 | Hartley et al. | |
| 2007/0055296 A1 | 3/2007 | Stergiopulos | |
| 2007/0142893 A1 | 6/2007 | Buiser et al. | |
| 2007/0142907 A1 | 6/2007 | Moaddeb et al. | |
| 2007/0168019 A1 | 7/2007 | Amplatz et al. | |
| 2007/0196423 A1 | 8/2007 | Ruane et al. | |
| 2007/0225785 A1 | 9/2007 | Park et al. | |
| 2007/0255149 A1 | 11/2007 | DeCampli | |
| 2008/0071343 A1 | 3/2008 | Mayberry et al. | |
| 2008/0140183 A1 | 6/2008 | Batiste | |
| 2008/0177368 A1 | 7/2008 | Goto | |
| 2008/0221666 A1 | 9/2008 | Licata et al. | |
| 2009/0018566 A1 | 1/2009 | Escudero et al. | |
| 2009/0149939 A1 | 6/2009 | Godlewski et al. | |
| 2011/0196712 A1 | 8/2011 | Sugimoto et al. | |
| 2011/0218613 A1 | 9/2011 | Leopold et al. | |
| 2012/0172965 A1 * | 7/2012 | Kratzberg | A61F 2/9661 |
| | | | 623/1.35 |
| 2013/0138139 A1 | 5/2013 | Stanley | |
| 2013/0289713 A1 | 10/2013 | Pearson et al. | |
| 2014/0188210 A1 | 7/2014 | Beard et al. | |
| 2019/0167408 A1 | 6/2019 | Harris et al. | |

FOREIGN PATENT DOCUMENTS

| | | |
|---|---|---|
| DE | 4427583 A1 | 2/1996 |
| DE | 19508129 A1 | 9/1996 |

(56) References Cited

FOREIGN PATENT DOCUMENTS

| | | | | |
|---|---|---|---|---|
| DE | 10105160 | * | 8/2000 | ............ A61F 2/92 |
| EP | 1072282 | A1 | 1/2001 | |
| GB | 1174814 | A | 12/1969 | |
| WO | 1988000455 | A1 | 1/1988 | |
| WO | 96/01597 | A2 | 1/1996 | |
| WO | 97/21402 | A1 | 6/1997 | |
| WO | 99/63907 | A1 | 12/1999 | |
| WO | 99/65420 | A1 | 12/1999 | |
| WO | 00/09047 | A1 | 2/2000 | |
| WO | 00/09048 | A1 | 2/2000 | |
| WO | 00/15158 | A1 | 3/2000 | |
| WO | 2000/042947 | A2 | 7/2000 | |
| WO | 2001005463 | A1 | 1/2001 | |
| WO | 2002/060345 | A2 | 8/2002 | |
| WO | 2004/002948 | A1 | 1/2004 | |
| WO | 2004066809 | A2 | 8/2004 | |
| WO | 2005/058201 | A1 | 6/2005 | |
| WO | 2006019626 | A2 | 2/2006 | |
| WO | 2007/001472 | A2 | 1/2007 | |
| WO | 2007127419 | A2 | 11/2007 | |
| WO | 2007084762 | A3 | 5/2008 | |
| WO | 2017/184153 | A1 | 10/2017 | |

OTHER PUBLICATIONS

National Institute of Diabetes and Digestive and Kidney Diseases, "Hemodialysis," (http://kidney.niddk.nih.gov/kudiseases/pubs/vascularaccess/#sec3), dated Jan. 2018.
U.S. Appl. No. 16/111,850, filed Aug. 24, 2018 Advisory Action dated Jul. 30, 2019.
U.S. Appl. No. 16/111,850, filed Aug. 24, 2018 Final Office Action dated Jun. 21, 2019.
U.S. Appl. No. 16/111,850, filed Aug. 24, 2018 Final Office Action dated May 4, 2020.
U.S. Appl. No. 16/111,850, filed Aug. 24, 2018 Non-Final Office Action dated Jan. 23, 2020.
U.S. Appl. No. 16/111,850, filed Aug. 24, 2018 Non-Final Office Action dated Mar. 19, 2019.
U.S. Appl. No. 16/111,850, filed Aug. 24, 2018 Notice of Allowance dated Jun. 18, 2020.

* cited by examiner

ADJUSTABLE VASCULAR GRAFT FOR CUSTOM INNER DIAMETER REDUCTION AND RELATED METHODS

PRIORITY

This application is a continuation of U.S. patent application Ser. No. 16/111,850, filed Aug. 24, 2018, now U.S. Pat. No. 10,765,504, which is a continuation of International Application No. PCT/US2017/064137, filed Dec. 1, 2017, each of which is incorporated by reference in its entirety into this application.

TECHNICAL FIELD

This disclosure pertains to prosthetic medical devices and, in particular, to an adjustable vascular graft that allows for a custom reduced inner diameter to be achieved by the end user and related methods.

BACKGROUND

Vascular grafts are prosthetic medical devices used in a variety of medical procedures, including for forming an anastomosis in the course of repairing or replacing diseased vessels, or for purposes of hemodialysis (which may involve forming an arteriovenous fistula, in which a vascular surgeon joins an artery and a vein together using such a graft). A typical graft is a flexible, elongated, tubular structure made of a biocompatible material, and thus designed to mimic the vessel(s) being repaired or connected. An example of a typical graft G is illustrated in FIG. 1, which is quite simply an elongated tubular or pipe-like structure that may have a variety of diameters and lengths depending on the intended use.

In the course of forming the anastomosis, it is sometimes desirable to create a reduced diameter section for regulating fluid flow through the graft, which may avoid creating circulatory problems in other parts of the vasculature. One past manner of achieving this reduction is for the vascular surgeon to cut the graft longitudinally along an intermediate portion, overlap the portions created by the cut, and stitch them back together to provide the entire graft with a desired reduction in diameter. Obviously, this is a laborious and time-consuming step in an otherwise medically complex procedure, potentially taking hours to complete, and is highly dependent on the skill of the vascular surgeon. Moreover, the resulting graft may produce sub-optimal results if the stitching becomes undone over time, or perhaps even if a tear results as a result of the weakening of the graft material resulting from the cutting required.

To avoid these limitations, a past proposal has been made for a so-called "flow restriction graft" F, an example of which is shown in FIG. 2. This graft is of the same tubular, flexible structure as illustrated in FIG. 1, but includes a necked portion N that provides the desired decrease in inner diameter (e.g., from 7 millimeters to 3 or 4 millimeters). While this device solves the above problems with manual reductions achieved by cutting the graft, it does not account for the possibility that a variety of reductions in diameter may be required, depending on the needs of a particular patient or use to which the graft is put. Obviously, if a different reduced diameter is desired than would be provided by a flow restriction graft on hand, then the manual reconstruction may be necessitated, which potentially leads to the aforementioned problems.

Accordingly, it would be desirable to provide an adjustable vascular graft that allows for a custom inner diameter reduction to be achieved by the end user in an easy and highly repeatable manner. The graft would thus be useful in a variety of applications, and avoid the past need for having different graft sizes on hand. It would also allow for the reduction in diameter to be achieved quickly, without the need for extensive reconstruction of the graft and the concomitant issues that may result.

SUMMARY

An object of the invention is to provide an adjustable vascular graft that allows for a custom inner diameter reduction to be selected by a clinician.

With that objective in mind, and according to a first aspect of the disclosure, a prosthetic medical device comprises a tubular graft having open ends and at least two rows of receivers formed in a substantially continuous sidewall thereof (which may be interrupted only by the receivers). The at least two rows of receivers are spaced apart in a circumferential direction about a continuous portion of the sidewall. A suture passes through the receivers, the suture having first and second ends. Tightening the suture, such as by pulling the first and second ends, cinches the graft, such that an inner diameter of the tubular graft is reduced. This provides the graft with a reduced flow portion, which may be selectively adjusted without the need for cutting the graft longitudinally to achieve a desired reduction in diameter.

In one embodiment, the at least two rows of receivers comprise a plurality of pairs of receivers, each pair of receivers spaced in an axial direction. The receivers in each pair may be aligned in the circumferential direction, and the receivers in each pair may be staggered in the axial direction.

The first and second ends of the suture extend from one receiver in each row. In one embodiment, the first end of the suture extends from an outermost receiver at a first end portion of the tubular graft and the second end of the suture extends from an outermost receiver at a second end portion of the tubular graft. In another embodiment, the first end of the suture extends from outermost receivers at the same ends of the at least two rows. The receivers may be provided along only an intermediate portion of the graft, such that an hourglass shape results from the cinching process.

The suture may pass through the receivers to form a crossing pattern. Alternatively, the suture may pass through the receivers to form a zig-zag pattern. In any case, the least two rows of receivers may include a first row of receivers and a second row of receivers, the first row of receivers spaced farther from a second row of receivers in a loosened condition of the suture and the first row is spaced closer to the second row of receivers in a tightened condition of the suture.

In any of the embodiments, each receiver may comprise an eyelet or a ringlet for receiving the suture. The eyelet may be oriented such that its axis is substantially perpendicular to an axial direction of the graft, and the ringlet oriented such that its axis is substantially parallel to the axial direction of the graft. The receiver may comprise a projection from a sidewall of the graft, such as a loop formed by another suture extending through the sidewall of the graft and anchored in place. The receivers may also be formed by a beading attached to the sidewall of the graft. The receivers may comprise holes formed in a reinforced region of the graft, which may be a thicker region or a sintered region of the sidewall of the graft.

In any of the foregoing embodiments, the suture may comprise a radiopaque material. The receivers may also comprise a radiopaque material. A mandrel may also be provided, the mandrel including a reduced diameter portion corresponding to a custom reduced diameter of the tubular graft, and may thus have an hourglass shape.

In any of the foregoing embodiments, the tubular graft may comprise expanded polytetrafluoroethylene ("ePTFE"), but other materials may also be used (e.g., an extracellular matrix, or "ECM")

According to a second aspect of the disclosure, a prosthetic medical device is provided. The device includes a tubular graft having open ends and an adjustable portion intermediate the open ends adapted for being reduced from a larger inner diameter to a smaller inner diameter for restricting flow through the tubular graft. In one embodiment, the adjustable portion includes a plurality of receivers (which may include eyelets) passing through a sidewall of the adjustable portion and connected by a suture (which may optionally comprise a radiopaque material), whereby tightening of the suture causes the adjustable portion to assume the smaller diameter. A mandrel may also be provided with a reduced diameter portion corresponding in size to a custom inner diameter of the tubular graft.

Still a further aspect of the disclosure pertains to a tubular graft comprising open ends and a sidewall including a plurality of receivers, which may comprise eyelets or ringlets. A suture may also pass through the plurality of receivers.

Yet another aspect of the disclosure pertains to a method of forming a tubular graft. The method comprises extending a suture through a plurality of receivers on the intermediate portion of the tubular graft, which when tightened reduces in inner diameter along at least a portion of the graft. The method may further include the step of inserting a mandrel having an outer diameter corresponding to a custom inner diameter of the intermediate portion into the tubular graft prior to the reducing step.

The method may further include the step of forming the rows of receivers in the graft by forming holes in a reinforced region of the graft. The method may also include forming the rows of receivers in the graft by creating projections from a sidewall of the graft. Still further, the method may include forming the rows of receivers by connecting eyelets, ringlets, or beading to a sidewall of the tubular graft.

BRIEF DESCRIPTION OF THE DRAWING FIGURES

The above and further advantages according to the inventions disclosed herein may be better understood by referring to the following description in conjunction with the accompanying drawings in which.

Figure 5:
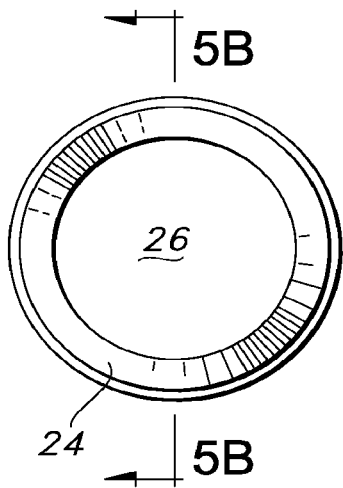
Figure 5A:
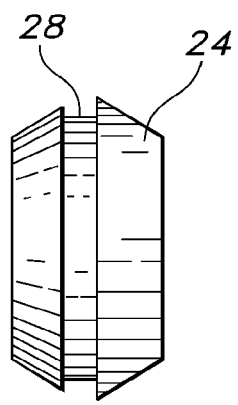
Figure 5B:
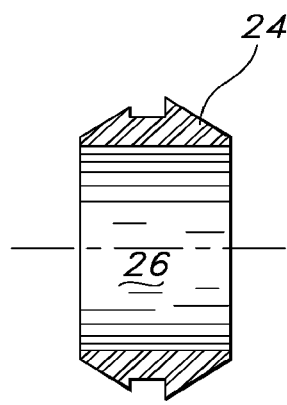
Figure 6:
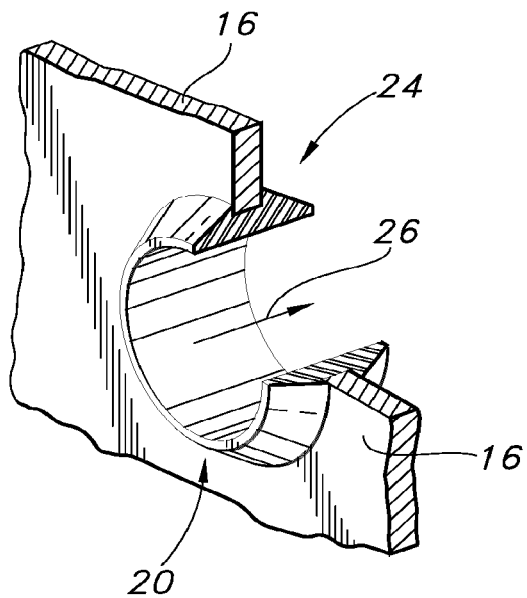
Figure 7:
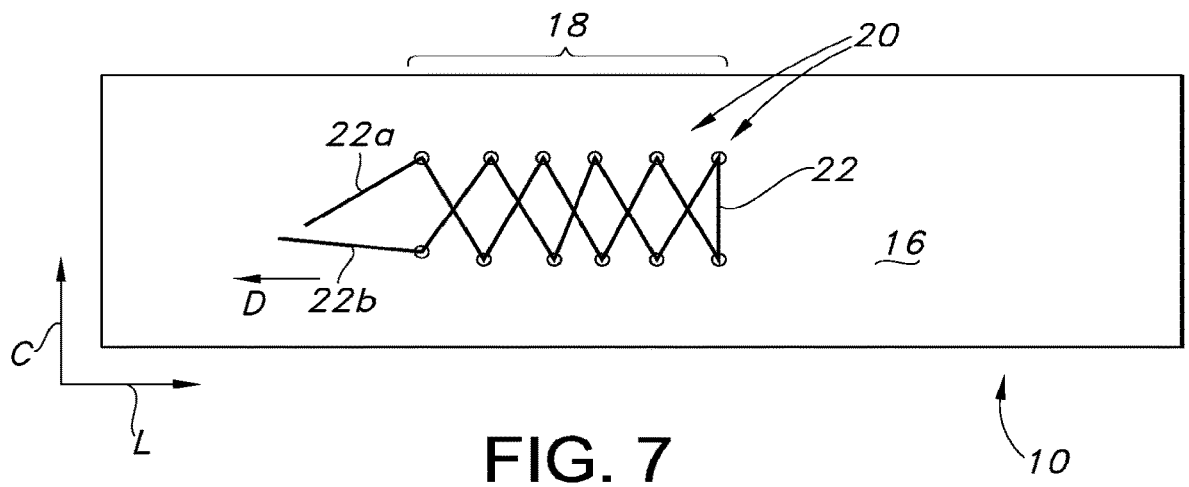
Figure 8:
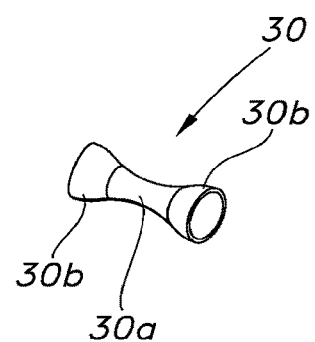
Figure 9:
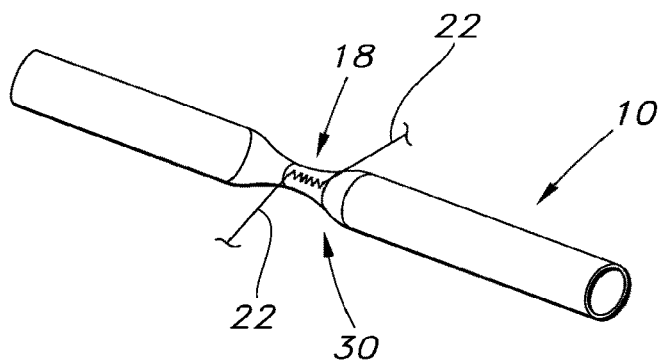
Figure 10:
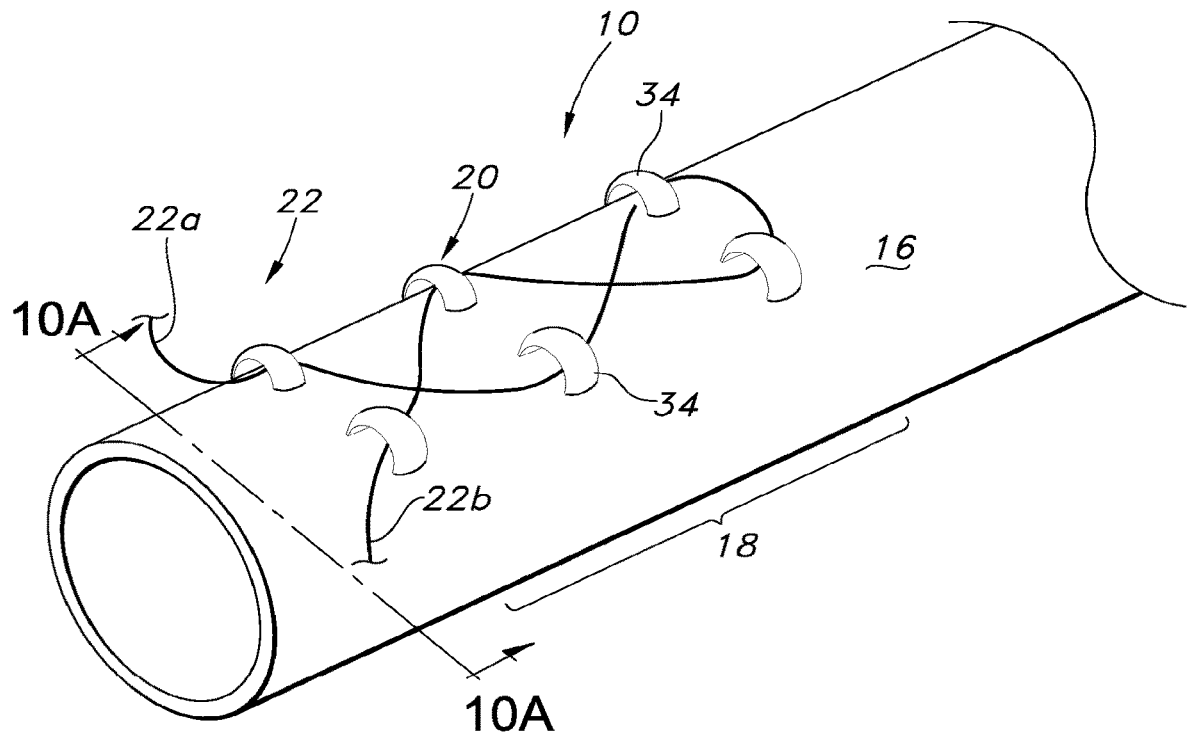
Figure 10A:
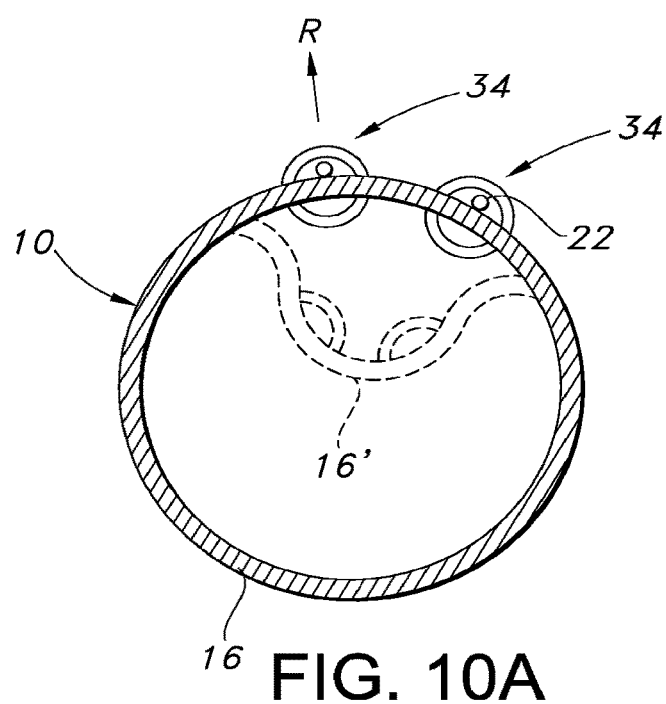
Figure 11:
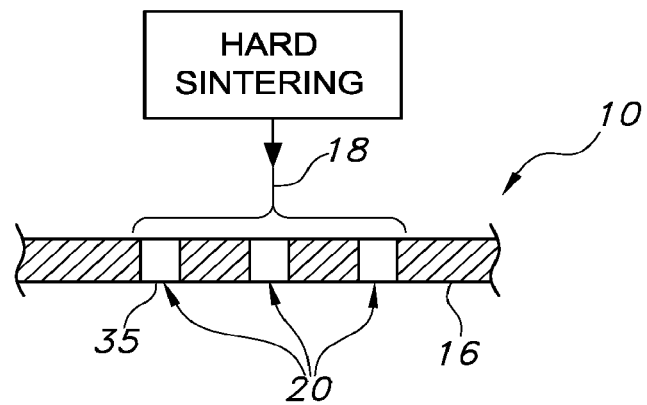
Figure 12:
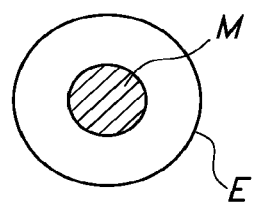
Figure 13:
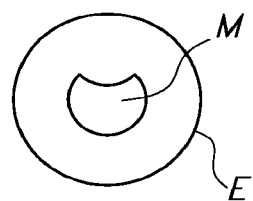
Figure 14:
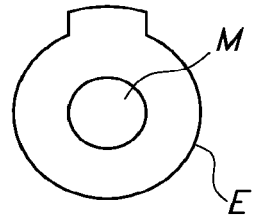
Figure 15:
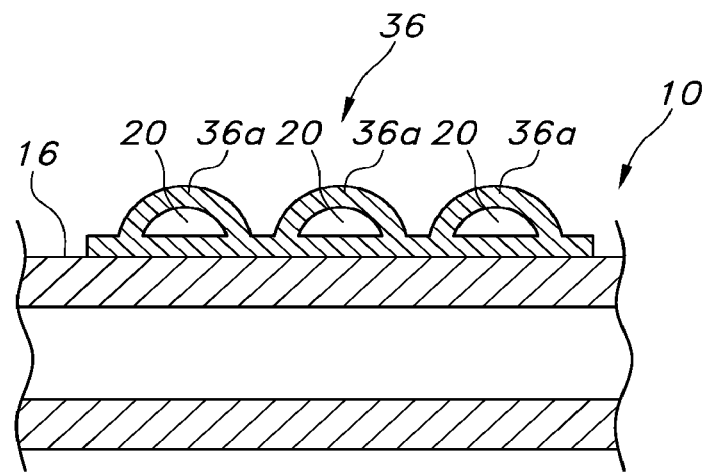
Figure 16:
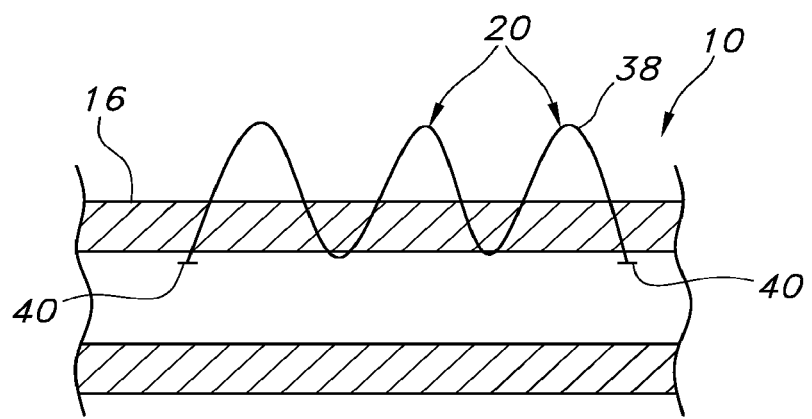

FIG. 5, 5A, and 5B are top, side, and cross-sectional views of an eyelet for optional use in connection with the adjustable graft;

FIG. 6 is a partially cutaway, partially cross-section view of an eyelet in the mounted condition;

FIG. 7 is a top view of an alternate embodiment of the adjustable graft according to the disclosure;

FIG. 8 is a perspective view of a mandrel according to another aspect of the disclosure;

FIG. 9 is an illustration of an adjustable graft with the mandrel therein and an associate suture in a tightened condition;

FIGS. 10 and 10A illustrate an alternate embodiment;

FIG. 11 is a partially cross-sectional view of a sidewall of the graft including holes formed in a reinforced region thereof;

FIG. 12 is a schematic view of a prior art die and mandrel arrangement for forming a tube having a continuous wall thickness;

FIGS. 13, and 14 are schematic views illustrating dies and mandrels for use in extruding a tube having a reinforced region;

FIG. 15 is a partly cutaway, partially cross-sectional view illustrating a beading attached to a sidewall of the graft to form receivers for receiving a suture; and FIG. 16 is a partly cutaway, partially cross-sectional view illustrating the use of a suture for forming the receivers.

The drawings are not necessarily drawn proportionally or to scale. For example, the dimensions of some of the elements may be exaggerated relative to other elements for clarity or several physical components may be included in one functional block or element. Further, sometimes reference numerals may be repeated among the drawings to indicate corresponding or analogous elements.

DETAILED DESCRIPTION

In the following detailed description, numerous specific details are set forth to provide a thorough understanding of the disclosed concepts. Those of ordinary skill in the art will know that the disclosed inventions may be practiced without these specific details. In other instances, well-known methods, procedures, components, or structures may not have been described in detail so as not to obscure the disclosed inventions.

The description provided below and in regard to the figures applies to all embodiments unless noted otherwise, and features common to each embodiment are similarly shown and numbered.

Figure 1:
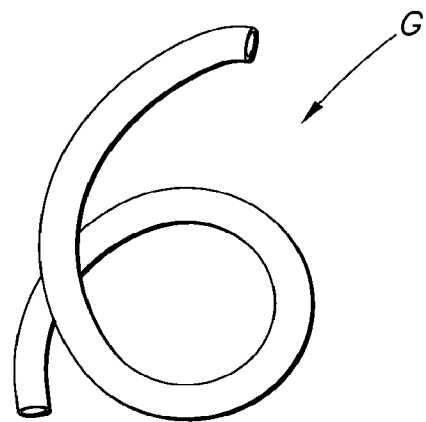
FIG. 1 is a perspective view of a prior art graft.
Figure 2:
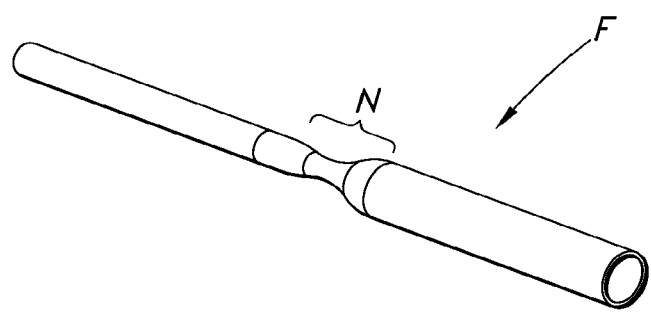
FIG. 2 is a perspective view of a prior art flow restriction graft having a reduced portion with a fixed diameter.
Figure 3:
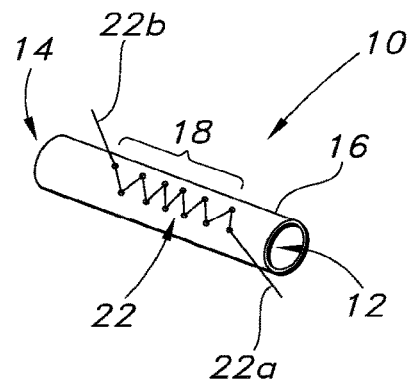
FIG. 3 is a top perspective view of an adjustable graft according to one aspect of the disclosure.
Figure 4:
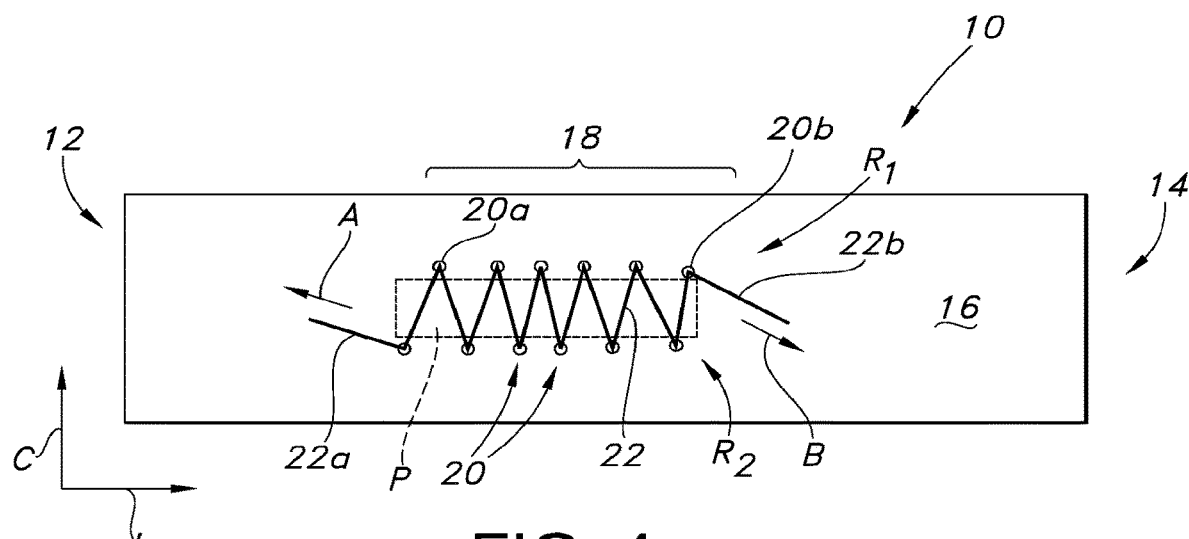
FIG. 4 is an enlarged top view of the graft of FIG. 1.

Referring first to FIGS. 3 and 4, one embodiment of an adjustable endovascular graft 10 is illustrated. The graft 10 includes a flexible, elongated tubular body having open ends or end portions 12, 14 and a sidewall 16. The open ends 12, 14 may be sized and shaped for connecting with other vessels, such as arteries, veins, other grafts, or any combination thereof (and which may be sutured in place to form a connection with the graft 10). The open ends 12, 14 may also be "cuffed," examples of which are the Distaflo® and Dynaflo® cuffed grafts distributed by Bard Peripheral Vascular, Inc. of Tempe, Arizona, and as described in US20100280598A1, the disclosure of which is incorporated herein by reference. The graft 10 may have any desired length or diameter and, as discussed in more detail below, may be fabricated from any of a variety of biocompatible materials to allow for endovascular use.

Between the open ends 12, 14 and spaced inwardly from them is an intermediate portion 18 of the graft 10, which is adapted to allow for adjustments to be made to the inner diameter along that portion of the graft to create a flow restricted passage. In one embodiment, the sidewall 16 along this intermediate portion 18 includes a plurality of receivers 20, which form openings through which a suture 22 may be laced. For example, as shown in FIG. 4, the receivers 20 may comprise pairs of receivers, which may be spaced apart in both the circumferential direction C and the axial or longitudinal direction L. In the illustrated embodiment, the receivers 20 are arranged in two generally parallel rows of receivers R1, R2, with the individual receivers staggered or offset in the circumferential direction, such that they do not align. As can be appreciated, the receivers 20 may be very small in size, and need only be sufficiently large to allow for the suture 22 to pass.

The suture 22 may be laced through the receivers 20 such that a first free end 22a extends from an outermost receiver 20a in one direction, and a second free end 22b extends from an outermost receiver 20b in the other (opposite) direction. Between the receivers 20a, 20b, a threaded portion of the suture 22 is arranged to form a "zig-zag" pattern, with alternating passes extending along the interior or exterior of the sidewall 16, respectively (that is, along the inner surface or the outer surface of the intermediate portion 18 of the graft 10 in alternating passes). As can be appreciated, the threading need not be through all receivers 20 provided, and the clinician may select the number of receivers to be used based on the desired length of the reduced diameter portion to be provided.

Thus, when the free ends 22a, 22b of the suture 22 extending from the outermost receivers 20a, 20b are pulled in opposite directions (as indicated by action arrows A and B). Consequently, the rows $R_1$, $R_2$ of receivers 20 are caused to move toward each other and become closer as a result of the shortening of the threaded portion of suture 22 in the tensioned condition (as compared to the suture in the loosened condition; compare FIGS. 3 (loosened) and 9 (tightened to provide graft 10 with "hourglass" shape). This tensioning results in a portion of the sidewall 16 bowing inwardly between the rows of receivers 20, which has the effect of reducing the inner diameter of at least the intermediate portion 18 of the graft 10 to create the desired flow restricted (intermediate) portion, and without altering the diameter of the end portions 12, 14. As can be appreciated, the sidewall 16 remains "substantially continuous" as a result (save for the small openings created by the receivers 20), with a strip P of uninterrupted material provided between the openings formed by the receivers 20.

As can be appreciated, the amount of reduction in diameter may be controlled by adjusting the amount to which the free ends 22a, 22b of the suture 22 are pulled in the respective directions. If the decrease is determined to be too great, as a result of a visual inspection, then tension on the free ends 22a, 22b may be released. Once the desired reduction is achieved, the position of the suture 22 may be fixed, such as by knotting, and the desired flow reduction achieved using the graft 10 with the reduced diameter intermediate portion 18. Of course, later adjustments can also be made by simply re-tensioning the suture accordingly.

To ensure the receivers 20 are sufficiently robust to handle the movement of the suture 22, they may optionally be provided with reinforcements, which in one form may comprise eyelets 24. As shown in FIGS. 5, 5A, and 5B, each eyelet 24 may comprise a generally circular structure formed of a rigid material (polymers or plastic, metal, suture material, or the like). The eyelet 24 has a hollow interior 26 for allowing the suture to pass freely, and an outer groove or channel 28, which may be adapted for receiving the material forming the sidewall 16, and thus securely retaining the eyelet in position. The eyelets 24 may thus be in the nature of grommets, and be retained purely by mechanical engagement with the surrounding sidewall 16, but security may be enhanced by the use of adhesives, welding (ultrasonic or heat) or other known alternatives for fastening two structures in a secure, biocompatible manner.

Alternative ways of forming the intermediate portion 18 with the adjustable inner diameter may be provided. For example, as shown in FIG. 7, pairs of receivers 20 in the sidewall 16 along the intermediate portion 18 may be generally aligned in the circumferential direction C and spaced in the axial direction L. The suture 22 may be laced through the receivers 20 in an intersecting or crossing manner, which each successive pass being interior to or outside of the sidewall 16. When the free ends 22a, 22b of the suture 22 are thus pulled in the same direction D, the rows of receivers 20 are drawn together, and the material of the graft 10 cinched along the intermediate portion 18 to the desired reduction in diameter.

While the reduction may be achieved in vivo, another possibility is to prepare the reduced diameter graft 10 prior to use. To facilitate this, a mandrel 30 may be provided, which includes a reduced diameter portion 30a that approximates the desired custom reduction in diameter to be achieved. In the illustrated embodiment, the reduced diameter portion 30a is bounded by larger diameter portions 30b, which still have an outer diameter that is at least slightly less than the inner diameter of the graft 10 (and which outer diameters may be the same or different for each portion 30b, depending on the application).

Thus, as indicated in FIG. 9, the mandrel 30 may be inserted into the graft 10 such that the reduced diameter portion 30a aligns with the intermediate portion 18 of the graft 10 in a "non-cinched" condition. The suture 22 may then be tensioned to reduce the inner diameter of the graft 10, but the amount of reduction will thus be limited by the outer diameter of the mandrel 30. The suture 22 may then be fixed, such as by tying, and the mandrel removed (such as by being dissolved or melted).

As an alternative, the mandrel 30 may be made in a modular fashion, which allows for the size of the reduced diameter portion 30a to be selected for a particular graft 10 or custom reduced inner diameter desired. The larger diameter portions 30b may be removably attached to the reduced diameter portion 30a, such as by using pins, to allow for easy assembly and disassembly (including for removing the mandrel 30 from the graft 10 once the custom inner diameter is realized). In perhaps the simplest form, the mandrel 30 may also comprise a cylindrical tube or rod having as its outer diameter the custom reduced inner diameter desired, about which the intermediate portion 18 would conform when cinched using the suture 22.

Reference is also made to FIGS. 10 and 10A, which illustrate an alternate embodiment in which the receivers 20 in the sidewall 16 are formed by projections therefrom. In the illustrated embodiment, the receivers 20 are provided by ringlets 34 at least partially embedded in the sidewall 16 and arranged in spaced rows. Similar to eyelets 24, the ringlets 34 may comprise rigid (metal) rings inserted through the sidewall 16, and could be co-molded with it, or the projections forming the receivers may be integrally formed in the sidewall (such as by molding). As shown in FIG. 10A, the ringlets 34 have a radial direction R that is aligned or substantially parallel to the radius of the graft 10, and a suture 22 thus passes through each ringlet along an axis thereof in a direction generally aligned with the axial direction L.

The ringlets 34 may receive the suture 22 in the manner shown, which is basically the intersecting configuration previously described. When the free ends 22a, 22b are pulled, the rows of ringlets 34 are moved closer together.

Consequently, the desired cinching effect and the reduction in diameter of the intermediate portion 18 is achieved (note collapsed portion of sidewall 16' indicated in phantom lines, which would be similar to that achieved in connection with the embodiments using eyelets 24). As can be appreciated, the ringlets 34 could be arranged differently to still achieve a cinching effect, such as the above-described "zig-zag" pattern by staggering the ringlets in the axial direction as well as the circumferential direction.

Other manners of forming the receivers 20 are also proposed. With reference to FIG. 11, holes 35 may be formed in the sidewall 16 of the graft 10, such as by using a hole punch or drill. The area immediately surrounding the holes 35 may then be reinforced. This reinforcement may be achieved by "hard sintering, or by applying pressure to the graft material surrounding the holes 35 during the sintering (heating without melting) process. The resulting material is denser, and thus stronger/stiffer. Consequently, the suture retention strength is increased along the intermediate portion 18 including the receivers 20, yet the rest of the graft 10 remains flexible and porous.

With reference to FIGS. 12, 13, and 14, the wall thickness in certain areas of the graft 10 may also be increased during the forming process by altering the shape of the die E and mandrel M. For a normal graft, as shown in FIG. 12, the die E inner diameter and the mandrel M outer diameter are both circular. The cross section of the resulting graft is the open space in between the two. Altering the shape of one of the mandrel M and or the die E, as shown in FIGS. 13 and 14, changes the thickness of the graft 10 in that region (but the same result could also be achieved by offsetting the mandrel M within the die E). Holes (not shown) may then be formed in the resulting tubular structure (such as by punching or drilling) to create the receivers. If desired, the sintering process may also be used in connection with this embodiment.

Still a further possibility is to use an external beading 36 on the graft 10 to form the receivers 20, as shown in FIG. 15. This beading 36 may be arranged along the graft 10 (such as in a spiral configuration) such that sections 36a of the beading 36 are raised above the material of the sidewall 16 to form the receivers 20 for the suture (not shown). The beading 36 may be attached in localized regions using the manufacturing process such that it is immovably attached (e.g. by welding or other bonding), and thus provides the desired points of retention for the suture. Two spaced rows of this beading 36 can be applied to achieve the desired rows of receivers 20. The beading 36 may also comprise a radiopaque material (e.g., metal or doped polymer) to allow for ready visualization under fluoroscopy.

Still another option is to form the receivers 20 of flexible material, such as a suture or suture-like material, as shown in FIG. 16. Specifically, a suture 38 can be sewn or laced through the material of the sidewall 16 to form the receivers 20. The ends of the suture 38 within the graft 10 may be mechanically anchored by anchors 40, such as knots or fasteners. Again, two circumferentially spaced rows of receivers 20 formed of suture 38 may be provided to allow for the cinching of the graft 10 and thus the desired at least partial reduction in inner diameter.

As can be appreciated, the maximum degree of cinching achieved may be controlled based on the spacing of the rows of receivers 20, with increased spacing achieving a greater reduction in diameter. For a typical case where the nominal inner diameter of the graft 10 is approximately 7 millimeters, and the desired reduction is to about 3-4 millimeters, the receivers could be spaced approximately 10-12 millimeters apart in the circumferential direction. Of course, a larger or smaller spacing could be used depending on the desired degree of reduction. Likewise, the length of the intermediate portion 18 including the receivers 20 may vary from what is shown in the drawings. An arrangement could be used in which not all receivers along the intermediate portion 18 receive the suture 22 (which means that, upon cinching, only part of the intermediate portion 18 would have the reduced diameter).

The vascular graft 10 according to the disclosure may be made of a variety of materials. Polytetrafluoroethylene (PTFE) has proven unusually advantageous as a material from which to fabricate blood vessel grafts or prostheses, because PTFE is extremely biocompatible, causing little or no immunogenic reaction when placed within the human body. In its preferred form of expanded PTFE (ePTFE), the material is light, porous and readily colonized by living cells so that it becomes a permanent part of the body. The process of making ePTFE of vascular graft grade is well known to one of ordinary skill in the art. The expansion of PTFE into ePTFE involves a controlled longitudinal stretching in which the PTFE is stretched to several hundred percent of its original length. Examples of ePTFE grafts are shown and described in U.S. Pat. Nos. 5,641,443; 5,827,327; 5,861,026; 5,641,443; 5,827,327; 6,203,735; 6,221,101; 6,436,135; and 6,589,278, each of which is incorporated in its entirety by reference. Grafts made from materials other than ePTFE that have been utilized include, for example, Dacron mesh reinforced umbilical tissues, bovine collagen, polyester knitted collagen, tricot knitted polyester collagen impregnated, and polyurethane (available under the trademark Vectra®). The graft 10 may also comprise an "extracellular matrix" or ECM, which may comprise the combination of one or more of collagen, proteins, proteoglycans, glycosaminoglycans, and other biological materials produced by cells that form the structural and functional components of all soft tissues and organs in the body.

The suture 22 may be fabricated of any known biocompatible suture material, such as polypropylene, Nylon (polyamide), polyester, PVDF, silk or metal (e.g., stainless steel). In one particular embodiment, the suture 22 may comprise a material that is radiopaque, which thus allows for the viewing of the suture under fluoroscopy. This may allow for a clinician to observe the condition of the suture 22 along the reduced diameter intermediate portion 18 of the graft 10 in vivo. The radiopaque material may be any of a variety of known radiopaque metals (e.g., platinum, stainless steel, gold, and tantalum, as examples), but may also comprise a polymer fiber having a radiopaque agent therein (e.g., Dyneema Purity® radiopaque fiber). A particular example of a radiopaque suture is also described in U.S. Patent Application Publication No. 2015/0327861, the disclosure of which is incorporated herein by reference.

The receivers 20 may also be made partially or fully radiopaque. In the case of the eyelet 24 or ringlet 34, this may be achieved by fabricating each from a radiopaque material, such as the above-referenced materials. Alternatively, radiopaque material may be embedded in a polymer material when forming the receiver 20 using any of the above-mentioned techniques. Making the suture 38 of the FIG. 16 embodiment radiopaque is also possible.

In summary, an adjustable vascular graft 10 is provided to create a custom reduction in flow along a portion of the graft. Specifically, the intermediate portion 18 of the graft 10 may achieve a reduction in inner diameter by tensioning a suture 22 passed through small receivers 20 in a sidewall 16, which may include reinforcements, such as eyelets 24, ringlets 34, holes 35, beading 36, or loops formed by a suture 38. A mandrel 30 may also be provide to help the vascular surgeon achieve a custom reduced inner diameter in a highly repeatable manner, and without the past need for cutting and repairing the graft 10 to achieve a reduction in diameter, which may save a great deal of time. The receivers 20 may be sufficiently small so as to avoid meaningfully compromising the strength or resilience of the graft 10. The need for stocking different sizes of grafts 10 is also eliminated, since a range of custom sizes may be created for a variety of applications. This improves the flexibility of use, and further reduces costs.

Each of the following terms written in singular grammatical form: "a", "an", and the", as used herein, means "at least one", or "one or more". Use of the phrase One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise. For example, the phrases: "a unit", "a device", "an assembly", "a mechanism", "a component, "an element", and "a step or procedure", as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase "consisting essentially of" Each of the phrases "consisting of and "consists of, as used herein, means "including and limited to". The phrase "consisting essentially of" means that the stated entity or item (system, system unit, system sub-unit device, assembly, sub-assembly, mechanism, structure, component element or, peripheral equipment utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional feature or characteristic" being a system unit system sub-unit device, assembly, sub-assembly, mechanism, structure, component or element or, peripheral equipment utility, accessory, or material, step or procedure, sub-step or sub-procedure), but only if each such additional feature or characteristic" does not materially alter the basic novel and inventive characteristics or special technical features, of the claimed item.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

Although the inventions of this disclosure have been illustratively described and presented by way of specific exemplary embodiments, and examples thereof, it is evident that many alternatives, modifications, or/and variations, thereof, will be apparent to those skilled in the art Accordingly, it is intended that all such alternatives, modifications, or/and variations, fall within the spirit of, and are encompassed by, the broad scope of the appended claims.

The following items also relates to the invention:

1. A prosthetic medical device, comprising:
    a tubular graft having open ends and at least two rows of receivers, the at least two rows of receivers being spaced apart in a circumferential direction along a substantially continuous portion, which is preferably continuous except for the receivers, of the sidewall; and
    a suture passing through the receivers;
    wherein the prosthetic medical device is configured such that tightening the suture reduces an inner diameter of the tubular graft.

2. The prosthetic medical device of item 1, wherein the at least two rows of receivers comprise a plurality of pairs of receivers, each pair of spaced in an axial direction.

3. The prosthetic medical device of item 1 or 2, wherein the receivers of each pair are aligned in the circumferential direction.

4. The prosthetic medical device of item 2 or 3, wherein receivers in each pair are staggered in the axial direction.

5. The prosthetic medical device of any of the preceding items, wherein first and second ends of the suture extend from one receiver in each row of receivers.

6. The prosthetic medical device of any of the preceding items, wherein a first end of the suture extends from an outermost receiver at a first end portion of the tubular graft and a second end of the suture extends from an outermost receiver at a second end portion of the tubular graft.

7. The prosthetic medical device of any of the preceding items, wherein first and second ends of the suture extends from outermost receivers at the same ends of the at least two rows.

8. The prosthetic medical device of any of the preceding items, wherein the suture passes through the receivers to form a crossing pattern.

9. The prosthetic medical device of any of the preceding items, wherein the suture passes through the receivers to form a zig-zag pattern.

10. The prosthetic medical device of any of the preceding items, wherein the at least two rows of receivers include a first row of receivers and a second row of receivers, the first row of receivers spaced farther from the second row of receivers in a loosened condition of the suture and the first row is spaced closer to the second row of receivers in a tightened condition of the suture.

11. The prosthetic medical device of any of items 1-10, wherein the entire sidewall is substantially continuous.

12. The prosthetic medical device of any of items 1-11, wherein the rows of receivers are provided on an intermediate portion of the tubular graft, optionally to create an hourglass shape when the suture is tightened.

13. The prosthetic medical device of any of items 1-12, wherein each receiver comprises an eyelet.

14. The prosthetic medical device of any of items 1-13, wherein each receiver is provided by a projection from the sidewall.

15. The prosthetic medical device of item 15, wherein the projection is created by a ringlet connected to the sidewall.

16. The prosthetic medical device of item 14 or 15, wherein the projection comprises a loop formed by another suture anchored to the sidewall of the tubular graft.

17. The prosthetic medical device of any of items 1-16, wherein the receivers are provided by a beading attached to the sidewall of the tubular graft.

18. The prosthetic medical device of any of items 1-17, wherein the receivers comprise holes formed in a reinforced region of the tubular graft.

19. The prosthetic medical device of item 18, wherein the reinforced region is a thicker region of the sidewall of the tubular graft.

20. The prosthetic medical device of item 18, wherein the reinforced region is a sintered region of the sidewall of the tubular graft.

21. The prosthetic medical device of any of items 1-20, wherein the suture comprises a radiopaque material.

22. The prosthetic medical device of any of items 1-21, wherein the receivers comprise a radiopaque material.

23. The prosthetic medical device of any of items 1-22, further including a mandrel including a reduced diameter portion corresponding to a custom reduced inner diameter of the tubular graft.

24. The prosthetic medical device of item 23, wherein the mandrel has an hourglass shape.

25. The prosthetic medical device of any of the preceding items, wherein the tubular graft comprises expanded polytetrafluoroethylene. The prosthetic medical device of items 1 to 25 may also have the features of items 26 to 36.

26. A prosthetic medical device, comprising:
a tubular graft having open ends and an adjustable portion intermediate the open ends configured for being reduced from a larger inner diameter to a smaller inner diameter for restricting flow through the tubular graft.

27. The prosthetic medical device of item 26, wherein the adjustable portion includes a plurality of receivers on either side of a continuous sidewall of the adjustable portion and connected by a suture, whereby tightening of the suture causes the adjustable portion to assume the smaller diameter.

28. The prosthetic medical device of item 26 or 27, wherein the suture comprises a radiopaque material.

29. The prosthetic medical device of any of items 26 to 28, wherein each of the plurality of receivers comprises an eyelet having an axis substantially perpendicular to an axial direction.

30. The prosthetic medical device of any of items 26 to 28, wherein each of the plurality of receivers comprises a ringlet having an axis substantially parallel to an axial direction.

31. The prosthetic medical device of any of items 26 to 30, wherein each of the receivers comprises a loop formed by another suture anchored to a sidewall of the tubular graft.

32. The prosthetic medical device of any of items 26 to 31, wherein the receivers are provided by a beading attached to the sidewall of the tubular graft.

33. The prosthetic medical device of any of items 26 to 32, wherein the receivers comprise holes formed in a reinforced region of the tubular graft.

34. The prosthetic medical device of item 33, wherein the reinforced region is a thicker region of the sidewall of the graft.

35. The prosthetic medical device of item 33 or 34, wherein the reinforced region is a sintered region of the sidewall of the graft.

36. The prosthetic medical device of any of items 26 to 35, further including a mandrel including a reduced diameter portion corresponding in size to a custom inner diameter of the tubular graft.

The prosthetic medical device of items 26 to 36 may also have the features of items 1 to 25.

37. A tubular graft comprising open ends and a substantially continuous sidewall including a plurality of receivers.

38. The tubular graft of item 37, further including a suture passing through the plurality of receivers.

39. The tubular graft of item 37 or 38, wherein the receivers comprise eyelets retained by the sidewall of the graft and having an axis generally transverse to an axis of the tubular graft.

40. The tubular graft of item 37 or 38, wherein the receivers comprises ringlets at least partially embedded in the sidewall of the tubular graft and having an axis generally aligned with an axis of the tubular graft.

41. The tubular graft of item 37 or 38, wherein the receivers comprise a loop formed by another suture extending through the sidewall of the tubular graft.

42. The tubular graft of any of items 37 to 41, wherein the receivers are provided by a beading attached to the sidewall of the tubular graft.

43. The tubular graft of any of items 37 to 42, wherein the receivers comprise holes formed in a reinforced region of the tubular graft.

44. The tubular graft of item 43, wherein the reinforced region is a thicker region of the sidewall of the tubular graft.

45. The tubular graft of item 43, wherein the reinforced region is a sintered region of the sidewall of the tubular graft.

46. A method of forming a tubular graft, comprising:
extending a suture through at least two circumferentially spaced rows of receivers provided on either side of a continuous portion of the tubular graft, whereby tightening the suture at least partially reduces an inner diameter of at least a portion of the tubular graft.

47. The method of item 46, further including the step of inserting a mandrel having an outer diameter corresponding to the reduced inner diameter of the intermediate portion into the tubular graft prior to the tightening step.

48. The method of item 46 or 47, further including the step of forming the rows of receivers in the tubular graft by forming holes in a reinforced region of the tubular graft.

49. The method of item 46, 47 or 48, further including the step of forming the rows of receivers in the tubular graft by creating projections from a sidewall of the tubular graft.

50. The method of any of items 46 to 49, further including the step of forming the rows of receivers comprises connecting eyelets, ringlets, or beading to a sidewall of the tubular graft.

The method of items 46 to 50 can be used for forming the tubular graft or prosthetic medical device of any of the preceding items.

What is claimed is:

1. A medical method, comprising:
obtaining a tubular graft having a continuous outer wall defining a first diameter along a longitudinal axis from a proximal end to a distal end, the tubular graft comprising:
a first set of receivers positioned in a first row along an intermediate portion of the tubular graft;
a second set of receivers positioned in a second row parallel to the first row along the intermediate portion of the tubular graft; and
a suture extending through the first set of receivers and the second set of receivers, the suture having a first free end and a second free end;
pulling the first free end and the second free end of the suture away from the first set of receivers and the second set of receivers to transition only the intermediate portion from the first diameter to a second diameter smaller than the first diameter, wherein a proximal portion and a distal portion of the tubular graft remain at the first diameter; and
fixing the first free end and the second free end of the suture to maintain the intermediate portion at the second diameter.

2. The method according to claim 1, further comprising inserting a mandrel into the tubular graft, the mandrel having an outer diameter corresponding to the second diameter of the intermediate portion prior to pulling the first free end and the second free end of the suture away from the first set of receivers and the second set of receivers.

3. The method according to claim 2, further comprising removing the mandrel after fixing the first free end and the second free end of the suture.

4. The method according to claim 3, wherein removing the mandrel comprises dissolving or melting the mandrel.

5. The method according to claim 2, wherein the mandrel is modular, further comprising selecting the outer diameter corresponding to the second diameter of the intermediate portion prior to inserting the mandrel into the tubular graft.

6. The method according to claim 1, wherein the first set of receivers and the second set of receivers of the tubular graft are integrally formed with the tubular graft via molding.

7. The method according to claim 1, wherein the first set of receivers and the second set of receivers of the tubular graft are selected from the group consisting of eyelets, ringlets, beading, and combinations thereof.

8. The method according to claim 1, wherein the first set of receivers and the second set of receivers of the tubular graft are circumferentially aligned.

9. The method according to claim 1, wherein the first set of receivers and the second set of receivers of the tubular graft are circumferentially staggered.

10. The method according to claim 1, wherein the first free end of the suture extends from an outermost receiver at a proximal end of the intermediate portion, wherein the second free end of the suture extends from an outermost receiver at a distal end of the intermediate portion, and wherein pulling the first free end and the second free end of the suture away from the first set of receivers and the second set of receivers comprises pulling the first free end of the suture toward the proximal end of the tubular graft and pulling the second free end of the suture toward the distal end of the tubular graft.

11. The method according to claim 1, wherein the first free end of the suture extends from an outermost receiver of the first set of receivers at a proximal end of the intermediate portion, wherein the second free end of the suture extends from an outermost receiver of the second set of receivers at the proximal end of the intermediate portion, and wherein pulling the first free end and the second free end of the suture away from the first set of receivers and the second set of receivers comprises pulling the first free end and the second free end of the suture toward the proximal end of the tubular graft.

12. The method according to claim 1, wherein the first free end of the suture extends from an outermost receiver of the first set of receivers at a distal end of the intermediate portion, wherein the second free end of the suture extends from an outermost receiver of the second set of receivers at the distal end of the intermediate portion, and wherein pulling the first free end and the second free end of the suture away from the first set of receivers and the second set of receivers comprises pulling the first free end and the second free end of the suture toward the distal end of the tubular graft.

13. The method according to claim 1, wherein pulling the first free end and the second free end of the suture away from the first set of receivers and the second set of receivers moves the first set of receivers circumferentially closer to the second set of receivers.

14. The method according to claim 1, wherein pulling the first free end and the second free end of the suture away from the first set of receivers and the second set of receivers creates an hourglass shape in the tubular graft.

15. The method according to claim 1, wherein the first set of receivers and the second set of receivers of the tubular graft comprise holes formed in a reinforced region of the intermediate portion of the tubular graft.

16. The method according to claim 15, wherein the reinforced region is a thickened region of the continuous outer wall of the tubular graft.

17. The method according to claim 15, wherein the reinforced region is a sintered region of the continuous outer wall of the tubular graft.

18. The method according to claim 1, wherein the suture comprises a radiopaque material.

19. The method according to claim 1, wherein the first set of receivers and the second set of receivers of the tubular graft comprise a radiopaque material.

20. The method according to claim 1, wherein the tubular graft comprises expanded polytetrafluoroethylene.

* * * * *